United States Patent [19]

Luly et al.

[11] Patent Number: 4,652,551
[45] Date of Patent: Mar. 24, 1987

[54] RENIN INHIBITING COMPOUNDS

[75] Inventors: Jay R. Luly, Lake Bluff; John J. Plattner; Joseph F. Dellaria, both of Libertyville, all of Ill.

[73] Assignee: Abbott Laboratories, N. Chicago, Ill.

[21] Appl. No.: 735,504

[22] Filed: May 17, 1985

Related U.S. Application Data

[63] Continuation-in-part of Ser. No. 623,742, Jun. 22, 1984, abandoned.

[51] Int. Cl.$^4$ .................. A61K 31/165; A61K 37/43; C07K 5/06; C07K 5/08; C07C 103/19
[52] U.S. Cl. ..................................... 514/18; 514/19; 514/616; 530/331; 564/152
[58] Field of Search .................. 260/112.5 R, 998.2; 530/331; 514/18, 19, 616; 564/152

[56] References Cited

U.S. PATENT DOCUMENTS

| | | | |
|---|---|---|---|
| 4,384,994 | 5/1983 | Veber et al. | 260/112.5 R |
| 4,424,207 | 1/1984 | Szelke et al. | 260/112.5 R |

FOREIGN PATENT DOCUMENTS

| | | |
|---|---|---|
| 0045665 | 2/1982 | European Pat. Off. |
| 0077028 | 4/1983 | European Pat. Off. |

OTHER PUBLICATIONS

Chem. Abstr. vol. 103, p. 54459v 198.
Journal of Medicinal Chemistry 28, No. 3 (1985), 263–273.
Journal of Chem. and Engineering 13, (1968) 450–451.
Kokubu et al., Biochemical and Biophysical Research Communications, 118, No. 3, 929–933 (1984).
Evin et al., Proceedings of the Eighth American Peptide Symposium, 583–586 (1984).
Johnson, J. Med. Chem., 23, 666–669 (1980).
Rodinger, Peptide Hormones, Parsons (ed.), U. Park Press, Baltimore, 1976, pp. 1–7.

Primary Examiner—Delbert R. Phillips
Attorney, Agent, or Firm—Steven F. Weinstock; Martin L. Katz

[57] ABSTRACT

The invention relates to renin inhibiting compounds of the formula $$(A)_n-B-\underset{R_1}{\overset{O}{\text{C}}}-\underset{R_2}{\text{N}}-\underset{}{\overset{R_3}{\text{C}}}-\underset{O}{\overset{}{\text{C}}}-\underset{R_4}{\text{N}}-\underset{R_5}{\overset{OH}{\underset{R_7}{\text{C}}}}-\underset{R_8}{\overset{}{\text{C}}}\underset{R_9}{\text{X}-R_6}$$

wherein A is an N-protecting group; n is 0 or 1; B is hydrogen, hydroxy, NH, loweralkyl or arylalkyl; with the proviso that when A is an N-protecting group, B is NH and when n is 0, B is hydrogen, hydroxyl, loweralkyl or arylalkyl; $R_1$, $R_3$ and $R_5$ are loweralkyl or hydrophilic, lipophilic or aromatic amino acid side chains and may be the same or different; $R_2$, $R_4$, $R_7$, $R_8$ and $R_9$ are hydrogen or loweralkyl and may be the same or different; X is $CH_2$; $R_6$ is loweralkyl, cycloalkyl, cycloalkylalkyl, aryl or arylalkyl; and X and $R_6$ when taken together may be a vinylic group.

11 Claims, No Drawings

RENIN INHIBITING COMPOUNDS

TECHNICAL FIELD

This application is a continuation-in-part of U.S. application Ser. No. 623,742 filed June 22, 1984.

The present invention relates to novel organic compounds which inhibit renin, a process for making such compounds, synthetic intermediates employed in these processes and methods of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotension system has been modulated or manipulated in the past, with ACE inhibitors. However, ACE acts on several substrates other than angiotensin I (AI), most notably the kinins which cause pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockage of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (*Nature,* Vol. 303, p. 81, 1983). In addition, Szelke and co-workers have described polypeptide analogs containing a non-peptide link (Nature, Vol. 299, p. 555, 1982) which also cause potent renin inhibition and show a high specificity for this enzyme.

DISCLOSURE OF THE INVENTION

In accordance with the present invention, there are renin inhibiting compounds of the formula

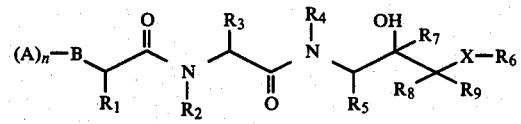

wherein A is an N-protecting group; n is 0 or 1; B is hydrogen, hydroxy, NH, loweralkyl or arylalkyl; with the proviso that when A is an N-protecting group, B is NH and when n is 0, B is hydrogen, hydroxy, lowerlalkyl or arylalkyl; $R_1$, $R_3$ and $R_5$ are loweralkyl or hydrophilic, lipophilic or aromatic amino acid side chains and may be the same or different; $R_2$, $R_4$, $R_7$, $R_8$ and $R_9$ are hydrogen or loweralkyl and may be the same or different; X is $CH_2$; $R_6$ is loweralkyl, cycloalkyl, cycloalkylalkyl, aryl or arylalkyl; and X and $R_6$ when taken together may be a vinylic group.

The preferable compound are when $R_2$, $R_4$, $R_7$, $R_8$ and $R_9$ are hydrogen, $R_1$ is benzyl, α- or β-naphthylmethyl, and $R_5$ is isobutyl or cyclohexylmethyl. The most preferable compounds are when $R_3$ is imidazole-4-yl-methyl, $R_5$ is cyclohexylmethyl and $R_6$ is loweralkyl.

The chiral centers of the compounds of the invention may have either the "R" or "S" configuration, but preferably have an "S" configuration.

The term "N-protecting group" as used herein refers to those groups intended to protect the N-terminus against undesirable reactions during synthetic procedures or to prevent the attack of exopeptidases on the final compounds or to increase the solubility of the final compounds and includes but is not limited to acyl, acetyl pivaloyl, t-butylacetyl, t-butyloxycarbonyl(Boc), carbobenzyloxycarbonyl(Cbz) or benzoyl groups; or an L- or D-aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "cycloalkyl" as used herein refers to an alicyclic residue containint 3-8 carbons and includes but is not limited to cyclohexyl and cyclopentyl.

The term "cycloalkylalkyl" as used herein refers to a cycloalkyl group as defined above appended to an alkyl radial of 1-4 carbons and includes but is not limited to cyclohexylmethyl and cyclopentylmethyl.

The term "aryl" as used herein refers to an phenyl, naphthyl, imidazole, pyrazole, indole or thiazole rings, unsubstituted or mono-substituted by halo or loweralkyl.

The term "arylalkyl" as used herein refers to an aryl group as defined above appended to an alkyl radical of 1-4 carbons.

The terms "lipophilic or aromatic amino acid side chains" as used herein refers to isobutyl, isopropyl, sec-butyl, benzyl, imidazole-4-yl-methyl, p-hydroxybenzyl,—and β-naphthylmethyl, (pyrazolyl)methyl, (thiazoyl)methyl, or cyclohexylmethyl or those other acid side chains which have an equivalent affinity for lipids or have an aromatic ring. The term "hydrophilic amino acid side chain" as used herein refers to serine, threonine, allothreonine, homoserine, cysteine, ornithine, arginine, or glutamine or those other amino acid side chains which have an equivalent affinity for water. General reference to amino acid side chains in both the description and claims herein is to be taken as reference to such, whether naturally occurring in proteins or not, and to both D- and L-forms.

The term "vinylic group" as used herein refers to a substituent of the formula $$-CR_{10}=CR_{11}R_{12}$$

wherein $R_{10}$, $R_{11}$ and $R_{12}$ are independently hydrogen or loweralkyl.

The terms "Ala", "His", "Leu" and "Phe" as used herein refer to alamine, histidine, leucine and phenylalamine, respectively.

The following Examples will serve to further illustrate preparation of novel compounds of the present invention.

EXAMPLE 1

A. 4-t-Butyloxycarbonylamino-3-hydroxy-6-methyl-1-phenylheptane

To a rapidly stirred −78° C. solution of Boc-Leucinal (1.50 g, 6.97 mmol) in anhydrous ether (10 ml) was added a −78° C. solution of phenethyl magnesium bromide (7 mmol) in anhydrous ether (40 ml) dropwise over the course of 15 minutes, and 45 minutes later the mixture was acidified. The oragnic phase was separated, washed with brine (2×10 ml) and dried (Na$_2$SO$_4$). Filtration and evaporation provided an oil (1.79 g) which was chromatographed with 150 g of 40 m SiO$_2$ (7/3, hexane/ether) to give the desired compound (0.17 g). Mass spectrum: M+ =321.

B. 4-Amino-3-hydroxy-6-methyl-1-phenylheptane hydrochloride

The resultant compound of Example 1 (87 mg, 0.27 mmol) was dissolved in methanol (1 ml) and was treated with methanolic HCl (5 ml of 0.75M). After 15 hours the solution was evaporated to provide the desired compound as a glass (71 mg) which was used without further purification.

C. Boc-Phe-Ala amide of 4-amino-3-hydroxy-6-methyl-1-phenylheptane

To a stirred −12° C. solution of Boc-Phe-Ala-OH (91.2 mg, 0.271 mmol) in anhydrous tetrahydrofuran (5 ml) was added N-methylmorpholine (30 μl, 0.271 mmol) and isobutylchloroformate (35 μl, 0.271 mmol) sequentially. After 3 minutes, a −12° C. solution of 4-amino-3-hydroxy-6-methyl-1-phenylheptane hydrochloride (0.271 mmol) in anhydrous tetrahydrofuran (3 ml) containing N-methylmorpholine (0.271 mmol) was added. Ten minutes later, the mixture was allowed to warm to room temperature for 2 hours, at which time the solvent was evaporated, and the resulting residue was partitioned between ethyl acetate (20 ml) and saturated NaHCO$_3$ (5ml). The organic phase was washed sequentially with 0.01M H$_3$PO$_4$ (5 ml) and brine (5 ml). Drying (Na$_2$SO$_4$) and evaporating provided 141 mg (96%) of crude material which was chromatographed on 1.5 g of 40 mm SiO$_2$ (98/2, dichloromethane/methanol) to give 106 mg (73%) of the desired compound. NMR (300 MHz, ppm in CDCl$_3$) 0.9 (m, 6H), 1.2–1.8 (m, 5H), 1.35 (d, 3H), 1.4 (s, 9H), 2.6–3.2 (m, 4H), 3.5–3.75 (m, 1H) 3.95 (m, 1H), 4.3 (m, 1H) 4.4 (m, 1H), 5.0 (m, 1H), 6.5–6.7 (m, 2H), 7.1–7.4 (m, 5H).

EXAMPLE 2

A. 4-t-Butyloxycarbonylamino-2,8-dimethyl-5-hydroxynonane

Using the procedure of Example 1A, but replacing phenethyl magnesium bromide with 2 equivalents of isoamyl magnesium bromide, gave the desired compound in 60% yield.

B. 4-Amino-2,8-dimethyl-5-hydroxynonane hydrochloride

Following the procedure of Example 1B and using the resultant compound of Example 2A, gave the desired compound.

C. Boc-Phe-Ala amide of 4-amino-2,8-dimethyl-5-hydroxynonane

Following the procedure of Example 1C and using the resultant compound of Example 2B, gave the desired compound.

EXAMPLE 3

Boc-Phe-His amide of 4-amino-2,8-dimethyl-5-hydroxynonane

A 250 mg portion of the product of Example 2B is partitioned between ether and 1N NaOH solution. The organic phase is dried over NaSO$_4$ and evaporated to give the free base, which is used without further purification.

To a stirred −23° C. solution of Boc-Phe-His-OH is added a solution of the above free base in dimethylformamide. Hydroxybenzotriazole (HOBT) and N',N'-dicyclohexylcarbodiimide (DCC) are then added sequentially. Afer 2.5 hours, the mixture is allowed to warm to room temperature for 16 hours, at which time the mixture is filtered and evaporated to a residue which is partitioned between ethyl acetate and saturated NaHCO$_3$. The organic phase is then washed separately with saturated NaHCO$_3$ and brine. Drying (Na$_2$SO$_4$) and evaporation of the solvent provides the crude product. Chromatography on SiO$_2$ eluting with dichloromethane-methanol mixtures gives the desired compound.

EXAMPLE 4

A. 5-t-Butyloxycarbonylamino-4-hydroxy-7-methyl-1-octene

Using the procedure of Example 1A, but replacing phenethyl magnesium bromide with allyl magnesium bromide, gave the desired compound in 52% yield. Mass spectrum: M+ =257.

B. 5-Amino-4-hydroxy-7-methyl-1-octene hydrochloride salt

Following the procedure of Example 1B and using the resultant compound of Example 4A, gave the desired compound.

C. Boc-Phe-Ala amide of 5-amino-4-hydroxy-7-methyl-1-octene

Following the procedure of Example 1C and using the resultant compound of Example 4B, gave the desired compound. Mass spectrum: $(M+H)^+ = 476$.

EXAMPLE 5

A. 5-t-Butyloxycarbonylamino-4-hydroxy-3,3,7-trimethyl-1-octene

Using the procedure of Example 1A, but replacing phenethyl magnesium bromide with 2 equivalents of 3-methylbut-2-enyl magnesium chloride gave the desired compound in 25% yield. Mass spectrum: $M^+ = 285$.

B. 5-Amino-4-hydroxy-3,3,7-trimethyl-1-octene hydrochloride salt

Following the procedure of Example 1B and using the resultant compound of Example 5A, gave the desired compound.

C. Boc-Phe-Ala amide of 5-amino-4-hyroxy-3,3,7-trimethyl-1-octene

Following the procedure of Example 1C and using the resultant compound of Example 5B, gave the desired compound in 89% yield. Mass spectrum: $M^+ = 503$.

EXAMPLE 6

A. 2-t-Butyloxycarbonylamino-1-cyclohexyl-3-hydroxy-6-methylheptane

Following the procedure of Example 2A, but replacing Boc-leucinal with Boc-cyclohexylalanal, gave the desired compound in 29% yield after chromatography. Mass spectrum: $M^+ = 327$.

B. 2-Amino-1-cyclohexyl-3-hydroxy-6-methylheptane hydrochloride salt

Following the procedure of Example 1B, and using the resultant compound of Example 6A, gave the desired compound.

C. Boc-Phe-His Amide of 2-Amino-1-cyclohexyl-3-hydroxy-6-methylheptane

Following the procedure of Example 3, but replacing the free base with the resultant compound of Example 6B and 1 equivalent of N-methylmorpholine, gave the desired compound in 63% yield after chromatography. Mass spectrum: $M^+ = 611$.

EXAMPLE 7

A. 1-Cyclohexyl-3-hydroxy-6-methyl-2-(methylamino)-heptane

To a stirred suspension of lithium aluminum hydride (LAH, 4 mmol) in tetrahydrofuran (THF, 15 ml) was added a solution of the resultant compound of Example 6A (1 mmol). The mixture was refluxed overnight, cooled, quenched sequentially with water (0.16 ml) and 3M NaOH (0.50 ml), filtered, dried, and evaporated to give the desired compound in 61% yield. Mass spectrum: $M^+ = 241$.

B. Boc-Phe-His amide of 1-cyclohexyl-3-hydroxy-6-methyl-2-(methylamino)heptane Following the proceudre of Example 3 using the resultant compouhd of Example 7A, gave the desired compound in 63% yield. Mass spectrum: $M^+ = 625$.

EXAMPLE 8

A. N,N (α,α)-Methyl, t-butyloxycarbonyl-N(π)-benzyloxymethyl-L-histidine

N(α)-t-Butyloxycarbonyl-N(π)-benzyloxymethyl-L-histidine [T. Brown, J. H. Jones, J. D. Richards, J. Chem. Soc. Perkin Trans. I, 1553 (1982)] was methylated according to the general procedure in J. R. McDermott and N. L. Benoiton, Can. J. Chem., 1915 (1973), to give the desired product.

B. N,N(α,α)-Methyl, t-butyloxycarbonyl-N(π)-benzyloxymethyl-L-histidine amide of 2-amino-1-cyclohexyl-3-hydroxy-6-methylheptane Following the procedure of Example 6C, but replacing Boc-Phe-His with the resultant compound of Example 8A, gave the desired compound.

C. N(α)-Methyl-L-Histidine amide of 2-amino-1-cyclohexyl-3-hydroxy-6-methylheptane dihydrochloride salt The resultant compound of Example 8B (100 mg) was dissolved in 1M anhydrous HCl in anhydrous methanol and was hydrogenated at 3 atmospheres $H_2$ with 30 mg of Pd black for 8 hours. Filtration and evaporation provided the desired compound (63 mg) which was used without further purification.

D. Boc-Phe-N(α)-methyl-L-His amide of 2-amino-1-cyclohexyl-3-hydroxy-6-methylheptane Following the procedure of Example 3, but replacing Boc-Phe-His with Boc-Phe and using the resultant compound of Example 8C with 2 equivalents of N-methylmorpholine, gave the desired compound. Mass spectrum: $M^+ = 625$.

EXAMPLE 9

A. (S)-2,8-Dimethyl-4-[(toluenesulfonyl)-amino]-S-nonanone

To a stirred $-78°$ C. solution of tosyl-Leu (Ts-Leu, 15 g, 53 mmol) in dry THF (240 ml) was added butyl lithium (57.8 ml of a 0.91M solution in hexane) followed 15 minutes later by isopentyl magnesium bromide (185 ml of a 0.8M solution in THF). The mixture was heated at reflux for 3 days, then cooled and poured into 0° 1M HCl (500 ml). The layers were separated and the aqueous phase was extracted with ether (3×150 ml). The combined organic layers were washed with saturated $NaHCO_3$ (2×150 ml) and brine (150 ml). Drying and evaporating provided a residue which was chromatographed on silica gel to give 7.43 g (41%) of the desired product. Mass spectrum: $(M+H)^+ = 340$.

B. 5-Hydroxy-4-(toluenesulfonyl)amino-2,5,8-trimethylnonane

To a stirred −78° C. solution of the resultant compound of Example 9A (1.25 g, 3.68 mmol) in dry THF (20 ml) was added methyl lithium (13.1 ml of a 1.4M solution in ether). The mixture was warmed to room temperature for 2 hours, cooled to 0°, and then quenched with 1M HCl (5 ml). The layers were separated, and the aqueous phase was extracted with ether (3×10 ml). The combined organic phase was was washed with saturated NaHCO$_3$ and brine, dried, evaporated, and chromotographed on silica gel to give 1.04 g (79%) of the desired product. Mass spectrum: (M+H)$^+$=356.

C. 4-Amino-5-hydroxy-2,5,8-trimethylnonane

To a solution of the resultant compound of compound 9B (205 mg, 0.577 mmol) in liquid ammonia (50 ml) was added sodium (207 mg, 9 mmol). After 5 hours the solvent was allowed to evaporate, and the residue was dissolved in benzene (30 ml) and ethanol (10 ml). The solvent was evaporated and the residue was partitioned between ether (20 ml) and water (20 ml). The ether phase was extracted with 2M HCl (2×5 mL), and the combined aqueous phase was made basic (pH 10) with 2M NaOH. Extraction with ether, drying the combined extracts, and evaporating gave 29 mg (25%) of the desired product. Mass spectrum: (M+H)$^+$=202.

D. Boc-Phe-Ala amide of 4-amino-5-hydroxy-2,5,8-trimethylnonane

Following the procedure of Example 1C using the resultant Compound of Example 9C, gave the desired compound in 61% yield. Mass spectrum: M$^+$=519.

EXAMPLE 10

A. 2-t-Butyloxycarbonylamino-1,5-dicyclohexyl-3-hydroxypentane

Following the procedure of Example 6A, but replacing isoamyl magnesium bromide with cyclohexylethyl magnesium bromide, gave the desired compound.

B. 2-Amino-1,5-dicyclohexyl-3-hydroxypentane hydrochloride salt

Following the procedure of Example 1B and using the result compound of Example 10A, gave the desired compound.

C. Boc-α-Nal-His amide of 2-amino-1,5-dicyclohexyl-3-hydroxypentane

Following the procedure of Example 3, but replacing the free base with the resultant compound of Example 10B and 1 equivalent of N-methylmorpholine and replacing Boc-Phe-His with Boc-α-Naphthylalanine-His, gave the desired compound.

EXAMPLE 11

A. 2-t-Butyloxycarbonylamino-1,6-dicyclohexyl-3-hydroxyhexane

Following the procedure of Example 6A, but replacing isoamyl magnesium bromide with cyclohexylpropyl magnesium bromide, gave the desired compound.

B. 2-Amino-1,6-dicyclohexyl-3-hydroxyhexane hydrochloride salt

Following the procedure of Example 1B and using the resultant compound of Example 11A, gave the desired compound.

C. Boc-Phe-His amide of 2-amino-1,6-dicyclohexyl-3-hydroxyhexane

Following the procedure of Example 3, but replacing the free base with the resultant compound of Example 11B and 1 equivalent of N-methylmorpholine, gave the desired compound.

EXAMPLE 12

A. 2-t-Butyloxycarbonylamino-1-cyclohexyl-3-hydroxy-6-phenylhexane

Following the procedure of Example 6A, but replacing isoamyl magnesium bromide with phenylpropyl magnesium bromide, gave the desired compound.

B. 2-Amino-1-cyclohexyl-3-hydroxy-6-phenylhexane hydrochloride salt

Following the procedure of Example 1B and using the resultant compound of Example 12A, gave the desired compound.

C. Boc-Phe-His amide of 2-amino-1-cyclohexyl-3-hydroxy-6-phenylhexane

Following the procedure of Example 3, but replacing the free base with the resultant compound of Example 12B and 1 equivalent of N-methylmorpholine, gave the desired compound.

EXAMPLE 13

A. Boc-His amide of 2-amino-1-cyclohexyl-3-hydroxy-6-methylheptane

Using the procedure of Example 6C, but replacing Boc-Phe-His with Boc-His gave the desired compound.

B. Dba-His amide of 2-amino-1-cyclohexyl-3-hydroxy-6-methylheptane

Using the procedure of Example 1B on the resultant compound of Example 13A, gave the corresponding deprotected material which was coupled with 2,2-dibenzyl acetic acid (Dba-OH) using the method of Example 6C to give the desired material.

EXAMPLE 14

Tba-Phe-His amide of 2-amino-1-cyclohexyl-3-hydroxy-6-methylheptane

Using the procedure of Example 13, but replacing 2,2-dibenzyl acetic acid with t-butylacetyl Phe (Tba-Phe), gave the desired material.

EXAMPLE 15

Pp-His amide of 2-amino-1-cyclohexyl 3-hydroxy-6-methylheptane

Using the procedure of Example 13B, but replacing 2,2-dibenzyl acetic acid with 3-phenylpropionic acid (Pp-OH) gave the desired compound.

EXAMPLE 16

Pl-His amide of
2-amino-1-cyclohexyl-3-hydroxy-6-methylheptane

Using the procedure of Example 13B, but replacing 2,2-dibenzyl acetic acid with L-3-phenyllactic acid (Pl-OH), gave the desired compound.

EXAMPLE 17

Mpp-His amide of
2-amino-1-cyclohexyl-3-hydroxy-6-methylheptane

Using the procedure of Example 13B, but replacing 2,2-dibenzyl acetic acid with 2(S)-methyl-3-phenylpropionic acid (Mpp-OH), gave the desired compound.

EXAMPLE 18

Boc-Ser amide of
2-amino-1-cyclohexyl-3-hydroxy-6-methylheptane

Following the procedure of 1C and replacing the free base with the resultant compound of Example 6B and employing Boc-Ser-OH in lieu of Boc-Phe-Ala-OH provided the desired compound. Mass spectrum: $M^+ = 414$.

EXAMPLE 19

Boc-Phe-Ser amide of
2-amino-1-cyclohexyl-3-hydroxy-6-methylheptane

Using the procedure of Example 1B and using the resultant compound of Example 18 gave the corresponding de-protected salt which was used below without further purification. Following the procedure of 1C, but replacing the free bas with the above salt and replacing Boc-Phe-Ala-OH with Boc-Phe-OH, gave the desired compound. Mass spectrum: $M^+ = 561$.

The compounds of the present invention can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptonate, hexanoate, hydrochloride, hydrobormide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lowerlalkyl halides, such as methyl, ethyl, propyl and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the present inhibition of renin is calculated. When tested in accordance with the foregoing procedure, the compounds of the invention demonstrated a high level of enzyme inhibition as seen in Table I.

The total daily dose administered to a host in single or divided doses may be in amounts, for example, from 0.001 to 10 mg/kg body weight and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

Injectable preparation, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In additon, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Suppositories for rectal administation of the drug can be prepared by mixing the drug with a suitable nonirritating excipient such as cocoa butter and polyethylene glycols which are solid at ordinary temperatures but liquid at the rectal temperature and will therefor melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

TABLE I

| Compounds (Example No.) | Inhibition |
|---|---|
| 1C | 35% at $10^{-5}$ $\underline{M}$ |
| 2C | 85% at $10^{-5}$ $\underline{M}$ |
| 3 | 89% at $10^{-5}$ $\underline{M}$ |
| 4C | 48% at $10^{-5}$ $\underline{M}$ |
| 5C | 7% at $10^{-5}$ $\underline{M}$ |
| 6C | 47% at $10^{-8}$ $\underline{M}$ |

We claim:

1. A renin inhibiting compound of the formula:

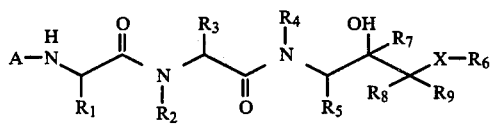

wherein A is a N-protecting group; $R_1$ is benzyl, α-naphthylmethyl, β-naphthylmethyl, phenethyl or p-methoxybenzyl; $R_3$ is imidazole-4-yl-methyl, benzyl, hydroxyloweralkyl or loweralkyl; $R_5$ is cyclohexylmethyl, benzyl, or loweralkyl; $R_2$, $R_4$, $R_8$ and $R_9$ are independently selected from hydrogen and loweralkyl; $R_7$ is hydrogen; X is $CH_2$; $R_6$ is selected from loweralkyl, cycloalkyl, cycloalkylalkyl, phenyl and benzyl; and X and $R_6$ when taken together may be a vinylic group; or pharmaceutically acceptable salts thereof.

2. The renin inhibiting compounds of claim 1 wherein $R_2$, $R_4$, $R_7$, $R_8$ and $R_9$ are hydrogen.

3. The renin inhibiting compounds of claim 2 wherein $R_1$ is benzyl.

4. The renin inhibiting compounds of claim 3 wherein $R_3$ is methyl.

5. The renin inhibiting compounds of claim 3 wherein $R_3$ is imidazole-4-yl-methyl.

6. The renin inhibiting compounds of claim 3 wherein $R_5$ is isobutyl.

7. The renin inhibiting compounds of claim 3 wherein $R_6$ is phenyl.

8. The renin inhibiting compounds of claim 3 wherein $R_6$ is isopropyl.

9. The renin inhibiting compounds of claim 5 wherein $R_5$ is cyclohexylmethyl and $R_6$ is isopropyl.

10. The renin inhibiting compound of claim 5 wherein A is Boc, $R_5$ is cyclohexylmethyl and $R_6$ is isopropyl.

11. A pharmaceutical composition for treating renin-associated hypertension, comprising a pharmaceutical carrier and a therapeutically effective amount of the compound of claim 1.

* * * * *